Figure 1:
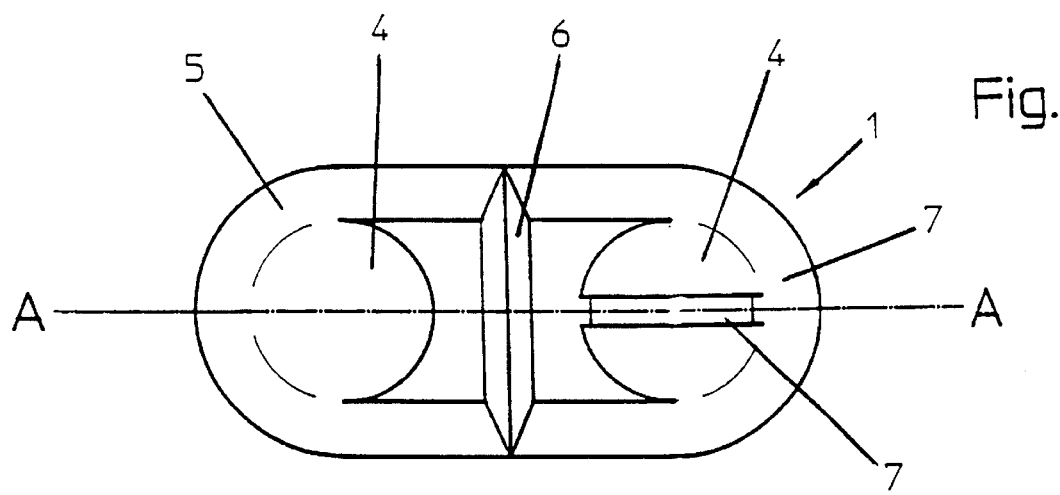

United States Patent
Demmer et al.

[11] Patent Number: 5,562,920
[45] Date of Patent: Oct. 8, 1996

[54] ELONGATED, DIVISIBLE TABLET

[75] Inventors: Fritz Demmer, Hirschberg; Rolf-Dieter Gabel, Schwetzingen; Walter Preis, Neustadt, all of Germany

[73] Assignee: Boehringer Manheim GmbH, Mannheim, Germany

[21] Appl. No.: 393,003

[22] PCT Filed: Aug. 19, 1993

[86] PCT No.: PCT/EP93/02218

§ 371 Date: Mar. 1, 1995

§ 102(e) Date: Mar. 1, 1995

[87] PCT Pub. No.: WO94/05949

PCT Pub. Date: Mar. 17, 1994

[30] Foreign Application Priority Data

Sep. 1, 1992 [DE] Germany .................... 42 29 085.6

[51] Int. Cl.⁶ ........................................... A61K 9/20
[52] U.S. Cl. ................ 424/464; D24/102; D24/101; D24/103

[58] Field of Search ............. 424/464; D24/102, D24/101, 103

[56] References Cited

U.S. PATENT DOCUMENTS

D. 210,371  3/1968  Kroninger et al. ............... 102/D24
D. 331,279  11/1992  Tovex ............................. D24/101

Primary Examiner—Thurman K. Page
Assistant Examiner—William E. Benston, Jr.
Attorney, Agent, or Firm—Nikaido, Marmelstein, Murray, Oram LLP

[57] ABSTRACT

Elongated, divisible tablet especially for pharmaceutical applications which, when the underside of the tablet is rested on a flat support, touches the support with two zones protruding from both ends of the underside of the tablet but not with the intervening zone wherein the protruding zones are formed as bulges. Such a tablet can be easily divided into two halves with one hand and picked up from a support. In addition it is easily manufactured.

17 Claims, 1 Drawing Sheet

# ELONGATED, DIVISIBLE TABLET

The invention concerns an elongated, divisible tablet especially for pharmaceutical applications which, when the underside of the tablet is rested on a flat support, touches the support with two zones protruding from both ends of the underside of the tablet but not the intervening zone. The underside of the tablet and the upper side of the tablet are defined as stated in W.A. Ritschel "Die Tablette" Editio Cantor KG, page 58, 1966.

In the development of solid pharmaceutical agents a search is made for forms of administration which can be manufactured particularly economically such as e.g. small round tablets. However, in practical use round tablets are found to have several disadvantages. The main problem, particularly for older persons, is the divisibility of such tablets. In many cases half the dosage is required in the initial phase of treatment (so-called "low initial" dose). The division is difficult because the breaking crevice is very fine and is easily overlooked or the patients do not know exactly how to divide the tablet. The result is two fragments of different sizes or even many small fragments. In addition one needs both hands for the division. In the case of older persons especially they additionally have particular difficulties in picking up small and light tablets from a support. It may therefore be the case that the patient asks the doctor for a form of administration which is easier to handle. These disadvantages are only negligibly less when the tablet has an oblong shape instead of a round shape.

There have been no lack of attempts at solving the problem of divisibility for example by using small apparatuses such as mini-guillotines. Such apparatuses are commercially available. However, the operation is complicated and the device must in each case be matched to the diameter of the tablet. A so-called kinked tablet was also developed. It has an angle shape—i.e. it is asymmetric—and therefore does not remain in the desired position on a support. Two hands are necessary to divide the kinked tablet. An additional disadvantage of this tablet is that it cannot be blister-packed on packaging machines. A small mechanical load leads to breakage of the tablet. A further embodiment of a divisible tablet is the Tiltab® sold by the SKB Company which can be easily picked up from a support. This is the case because when this tablet is placed on a support it always stands up on one side due to its geometry. Due to its length (14 mm) and its oval shape, the tablet is relatively easy to divide. However, the oval shape especially is a great disadvantage on a packaging machine because an oval tablet can get wedged on the feeding rails. Moreover, the manufacture of the compression tools is complicated and expensive.

In addition tablets are known which are shaped so that their middle zone is thinner than two opposite end zones positioned on a straight line running through the middle zone and preferably have a breaking crevice through their middle zone which is perpendicular to the said straight line. When the tablet is halved the said end zones of the tablet lie on the support while the middle zone is spaced from the support. The tablet is divided into two halves by lever action by pressing a finger on its middle zone towards the support.

Such a tablet which preferably has a round shape is described in EP 0 207 888. The round shape is in fact advantageous with regard to processing in particular during pressing and when providing a coating. However, round tablets are inferior to elongated tablets with regard to their divisibility since much force has to be used for bisecting because the lever arm is relatively short and the fracture surface is relatively large. An elongated tablet of this type in which the tablets rest on the support during division with a line vertical to the line connecting the ends or with a narrow surface, is described in the U.S. Pat. No. 5,061,494. Due to the shape of the zones on which the tablet rests on the support, the tablet has an almost rectangular shape. Another elongated tablet of this type is described in the U.S. Pat. No. 4,735,805. This tablet is composed of an elliptical plate on both sides of which frustoconical-like elevations are provided in which a groove with a round profile is provided extending perpendicular to the longitudinal axis in such a way that in each case the deepest point of the groove is approximately in the geometric middle of the plate and at both ends a ridge runs across an apex i.e. the frustoconical elevations have a concave concavity. Although the tablets described in both US patents have advantages over the tablet described in EP 0 207 888 with regard to divisibility, they have disadvantages in the manufacture in particular with regard to coating which is apparently related to the fact that they deviate relatively strongly from a round convex form, the tablet described in the U.S. Pat. No. 4,735,805 differing from a round convex form not only in the oblong form but also in the concave indentation. The latter tablet also tends to wedge on the feeding rail of the packaging machines due to its elliptical shape.

The ability to package a tablet efficiently and to provide it with a coating are important cost criteria in tablet manufacture because coating with a film in particular has to be carried out very often in order to for example cover up a bad taste or a rough surface of the tablet or to apply a retarding film. A prerequisite for the problem-free manufacture of the coating is that these rotate (roll) perfectly in the coating tank in addition to the coating composition and the quality of the tablets to be coated. In practice only round convex tablets rotate without difficulty. In contrast tablets whose shape differs strongly from a round convex shape such as for example conventional oblong tablets do not roll satisfactorily. These oblong tablets which have the shape of a flat plate with two large surfaces with straight longitudinal sides running parallel to one another and perpendicular to the large surfaces and with round ends, are not provided with a uniform coating during coating. In addition they get caught together on the wall of the coating tank and form structures which are similar to a net. As a result they are pulled up the tank wall and break up far above the core bed then to fall back into the core bed. In larger coating tanks the drop height is so large that the tablets can break in this process. Also the movement within the core bed is more a sliding than a rolling. Indeed it is often the case that the tablets do not rotate at all but rather "slide through". It is therefore not inevitable that the tablets are coated inhomogeneously which can be seen with the naked eye particularly in the case of coloured film tablets. If, in contrast, the tablets have the property of rolling, the coating is uniform. The object of the invention is therefore to provide a tablet which does not have the aforementioned disadvantages. In particular it should roll well in a coating tank, be simple to manufacture and coat and if desired, be divisible so that it can be handled and bisected without difficulty by older or visually handicapped people.

This object is achieved with a tablet of the type described in the introduction in which the protruding zones are in the shape of bulges.

The tablet according to the invention has important advantages with regard to divisibility and grippability over the tablets described in the three aforementioned documents. In particular the tablet according to the invention can be handled and bisected with ease and is in addition simple to manufacture and coat. Thus it was found that the new tablet form rolls perfectly in the bed of a coating tank i.e. it behaves like a round convex tablet and can thus be provided with a uniform coating without difficulty. That was not predictable. A further advantage is that the tablet according to the invention has a relatively large volume in relation to its surface so that it has smaller dimensions than other tablets with the same volume.

It is advantageous when the tablet has a dumb-bell shape i.e. has a shape which is axially symmetric to the longitudinal axis of the tablet because it can then be divided by finger pressure into two halves in any position relative to the support. A tablet shaped thus can also be easily picked up by its middle zone which is always spaced from the support independent of its position relative to the support.

A tablet is also advantageous which is designed in such a way that the upper side of the tablet is designed in the same way as the underside of the tablet. When this embodiment of the tablet according to the invention is halved, the convex shaped bulges have the advantage over the concave design described in U.S. Pat. No. 4,735,805 that the pressing finger slides automatically to the lowest point i.e. to the middle of the tablet where it is intended to divide it. This is very helpful particularly in the case of older patients whose vision is limited since this greatly simplifies the handling by such patients.

An advantageous embodiment of the tablet according to the invention in which the underside of the tablet and if desired, also the upper side of the tablet is shaped in the aforementioned manner, has a flat plate wherein the bulges protrude from one or both of the large plate surfaces which are opposite to one another.

It is advantageous for the fabrication of the tablet when the plate has the shape of an oblong with approximately semi-circular end zones and lateral edges parallel to the longitudinal axis in the middle zone of the tablet (1), the distance between the edges parallel to the longitudinal axis preferably being the same as, but if desired also smaller or larger, than the diameter of the semicircles at the ends of the oblong whereby if the distance is smaller the circular sectors are larger than a semicircle. The compression tools required to produce such a tablet are simpler to manufacture like those for conventional oblong tablets. In addition a good guidance on packaging machines is ensured by the lateral edges parallel to the longitudinal axis in the middle zone of the tablet. In addition, in contrast to conventional oblong tablets, the tablets according to the invention shaped in this manner do not have a tendency to hook together and to form net-like structures with the aforementioned disadvantages during coating in the coating tank despite the oblong-shaped plate. The tablet according to the invention designed in this way is thus very advantageous not only in the tablet manufacture but also in the further processing i.e. in coating and/or packaging. Moreover the tablet according to the invention with an oblong-shaped plate has smaller plate dimensions than a conventional oblong tablet of the same volume that does not have convex bulges. In addition the tablet looks subjectively to be smaller and thus less "threatening" than a conventional oblong tablet with a plate of the same size.

It is favourable in the case of the tablet with an oblong-shaped plate that the bulges form spherical segments at least in the area of the apexes. The tablet is particularly easy to handle when the sphere diameter of the spherical segments is larger than the height (dimension perpendicular to the large surfaces of the plate) of the tablet because, when its two spherical segments have contact with a flat support, it positions itself automatically on the support in such a way that the large surfaces of the plate are positioned approximately parallel to the support i.e. they are in an advantageous position for division. Contact of the spherical segments with the support is almost automatic when the largest dimension (width) of the large surfaces perpendicular to the longitudinal axis of the tablet is larger than the height of the tablet. In order to further facilitate the divisibility it is advantageous when the tablet has at least one breaking crevice in its middle zone which is approximately perpendicular to the line connecting the end zones of the tablet with which the tablet rests on a support during division.

In a preferred embodiment of the tablet according to the invention the semicircular end zones of the tablet halves usually rest on the support after the division whereas the fracture edge points obliquely upwards. As a result the halves can be very easily grasped and lifted from the support. This advantageous position is not assumed by the tablet halves in all cases if—which is easy to avoid—the centre of gravity of the tablet halves lies on the connecting line between the apexes of each tablet half.

In a further advantageous design of the tablet a groove runs over the apex of at least one of the bulges the projection of which on one of the large surfaces of the plate forms either no or at most an acute angle with the longitudinal axis of the tablet. The depth of the groove may also be zero. It is possible to accomodate a name, e.g. the logo—or a part thereof—of the tablet manufacturer in such a groove. The edges which the groove forms with the surface of the bulge preferably run approximately mirror-symmetrically to a plane standing approximately perpendicularly to the plate. When a tablet with groove edges that run in this manner touches a flat support it has an even more stable hold on the support than when only its intact spherical surface touches it. This also additionally simplifies its divisibility. A similar stable standing position of the tablet on the support is achieved when the apex of at least one of the bulges forms a small surface parallel to the large surfaces of the plate.

The tablet according to the invention is particularly suitable as a pharmaceutical form of administration for any active substances. Any desired pharmaceutical active substance can be used as the active substance, for example chemotherapeutic agents, phytopharmaceutical agents, vitamins, enzymes, hormones etc..Bezafibrate, clodronic acid, Carvedilol or Glibenclamide are mentioned as examples of active substances. The active substances can be present in any desired dosage, for example of 0.1–100 % by weight of the tablet core. If the active substances can be pressed directly into tablets without further pharmaceutical auxiliary or carrier substances, the tablet according to the invention can also be composed of the pure active substance. However, further auxiliary or carrier substances are usually used for the manufacture such as for example filling agents, tablet disintegrants, lubricants or mould release agents, binding agents, adsorbents, dissolution retarders, agents which increase the hydrophilicity, flow-regulating agents, absorption accelerators, taste corrigents or colourings.

The tablets are preferably manufactured from a granulate which has been produced by dry, wet or spray granulation of the tablet components or by compaction.

Further advantageous embodiments of the tablet according to the invention are disclosed in the subclaims.

Figure 2:
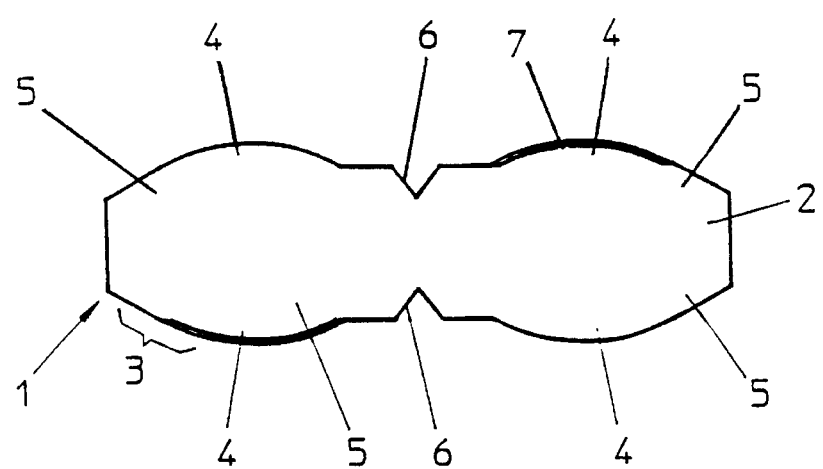
Figure 3:
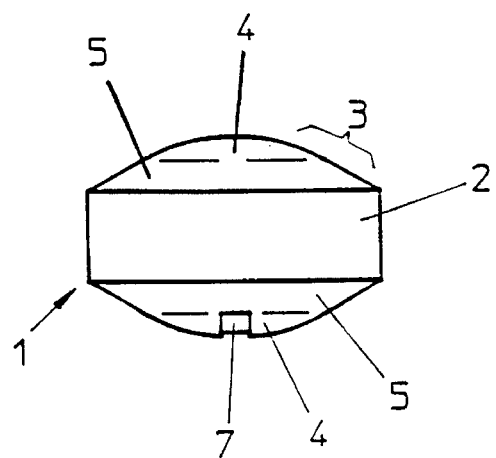

The invention is described on the basis of examples of design illustrated by drawings. FIG. 1 shows an enlarged diagram in a top view of an embodiment of the tablet according to the invention which rests on a horizontal support in a suitable position for the bisection. FIG. 2 shows a longitudinal section through the tablet shown in FIG. 1 along the lines A—A drawn in FIG. 1. FIG. 3 gives a view towards the longitudinal axis of the tablet shown in FIG. 1 and 2.

The tablet 1 illustrated in FIG. 1 to 3 has all essential and advantageous features of the invention. It should, however, be made clear that although the tablet illustrated by the Figures represents the most preferred embodiment, other embodiments of the tablet according to the invention encompassed by the scope of the claims can be used advantageously due to their economical fabrication and/or good handling.

FIG. 1 shows an oblong, i.e. a structure, which is composed of a circle cut into two halves and a rectangle which is inserted between the edges of cut and whose sides facing the semicircles are of the same length as the diameter of the circle. The oblong forms the surface area of a plate 2. Plate 2 has three planes of symmetry C, D and E. The planes of symmetry C and D are perpendicular to the parallel-spaced large surfaces of plate 2 and the plane of symmetry E is parallel to the large surfaces. The longitudinal axis of tablet 1 extends along the line of intersection of the planes of symmetry C and E. The longitudinal section shown in FIG. 2 coincides with the plane of symmetry C and the cross section shown in FIG. 3 is parallel to the plane of symmetry D. Each of the two large surfaces of plate 2 have two bulges 3. Perpendicular projections of the apexes of the bulges 3 onto the plate 2 coincide with the circle centres of the semicircles. In the apex region the bulges 3 are in the form of spherical segments 4. The transition between the spherical segments 4 and the plate 2 is formed by two plates 5 whose surfaces adjoining the large areas of the plate 2 are congruent with the oblong and taper towards the spherical segments 4 so that the plates 5 continuously merge into the spherical segments 4 in the area of the semicircular ends. It should be made clear that the division of the tablet into plates 2 and 5 and spherical segments 4 only serves to unequivocally describe the tablet. In reality these shaped elements form a unit which is produced in one pressing process.

The sphere diameter of the spherical segments 4 i.e. the diameter of the spheres of which the spherical segments form a part is larger than the height of the tablet. This makes the tablet particularly easy to handle because when its two spherical segments make contact with a flat support it positions itself automatically on the support in such a way that the large areas of the plate are aligned approximately parallel to the support. The contact of the spherical segments with the support is almost automatic when, in a preferred embodiment of the tablet, the largest dimension (width) of the large areas perpendicular to the longitudinal axis of the tablet is larger than the height of the tablet. The plates 5 are each divided into two equal halves by the wedge-shaped breaking crevice 6 which runs symmetrically to the plane of symmetry D.

A groove 7 of rectangular cross section is provided in one of the spherical segments 4 on each of the two sides of plate 2 mirror-symmetrically to the plane of symmetry C. The bottom of the groove 7 can carry the logo—or a part thereof—of the company who manufactures or sells the tablet.

The length of the oblong is typically about 17 and its width about 8 mm and the bulges 3 each have a height of about 1.5 mm with a total height (distance between two apexes of the bulges that are mirror-symmetrical to the plate 2) of about 5.5 mm. The length of the tablet should be such that the finger pressure during division does not act on the apexes of the bulges but rather on the region between.

The described tablet 1 has advantageous properties. If the tablet rests on a flat support such that the large areas of the plate 2 are aligned parallel to the support and the spherical segments 4 on one side of the plate touch the support—a position which the tablet will automatically assume as described above—then the middle zone of the tablet has no contact with the support. The tablet can therefore easily be gripped there and lifted. The described position of the tablet is additionally stabilized by the groove 7 because the edges which the groove 7 forms with the surface of the sphere run approximately mirror-symmetrically to a plane which is approximately perpendicular to the plate 2. Due to the lack of contact of the middle zone with the support, the tablet can be divided without effort in the described position even without aids. For this one only has to exert pressure from above on the middle zone with a finger. The middle is the place with the maximum bending moment i.e. that site at which the tablet can be divided with the least exertion.

In contrast to conventional round or oblong-shaped tablets, the tablet does not have to be held in the hand when it is broken. The two spherical segments 4 on the side of the plate facing away from the support automatically lead the finger with which the pressure is exerted to the middle of the tablet. Therefore people with limited vision can also divide the tablet without any aids. After the division the fracture edges of the tablet halves rest on the support while the semicircular end zones point diagonally upwards. As a result the halves can be easily gripped and lifted from the support. In addition the tablets can be easily provided with a uniform coating by rolling in a coating tank. Thus despite the straight side walls in the middle tablet zone which run parallel to one another, it behaves like a round convex tablet. Due to these straight side walls it is also possible to guide the tablet in packaging machines without getting wedged. In addition the tablet has a relatively large ratio of volume to outer surface and is thus smaller with regard to its outer dimensions than for example conventional oblong tablets of the same volume. Moreover the tablet also looks subjectively smaller than a conventional oblong tablet which has the same dimensions as the plate 2.

Embodiments of the tablet according to the invention are also usable which have shapes that are different to that of the tablets described in the Figures even when they may not have all of the described advantages. For example the tablet can have other dimensions or another length: width: height ratio. It is also possible that the quadrangle between the semicircular ends is narrower than the diameter of the circle i.e. the tablet assumes a dog-biscuit form. The tablet can also be shaped like a dumb-bell. On the other hand shapes can also be used in which either the plates 5 which taper towards the spherical segments 4 are not present or the bulges 3 are completely absent on one side of the plate 2. If the bulges 3 of a tablet of the latter shape are laid on a support, the good divisibility is indeed given as before but the advantage that the finger is automatically led to the middle is absent.

We claim:

1. Elongated, divisible tablet having an underside, a topside, a longitudinal axis, two ends and an intervening zone therebetween, the underside when resting on a flat surface touching the flat surface at two bulges protruding from proximate both ends of the underside but not from the intervening zone.

2. Tablet of claim 1, wherein the tablet in a cross-section is in the form of a dumbbell.

3. Tablet of claim 1, wherein the topside of the tablet is generally of the same configuration as the underside.

4. Table of claim 1, wherein the tablet comprises a flat plate having large plate areas, the large plate areas having bulges protruding therefrom proximate the ends at least on the tablet underside.

5. Tablet of claim 4, wherein the bulges protrude from the large plate areas on both the topside and the underside of the table.

6. Tablet of claim 4, wherein the large areas of the plate are in the shape of an oblong with semi-circular end zones defining diameters thereof, the large areas of the plate having lateral edges parallel to the longitudinal axis of the tablet, the distance between the lateral edges being substantially the same as the diameters of the semicircles at the ends of the oblong.

7. Tablet of claim 4, wherein the large areas of the plate are in the shape of an oblong with rounded end zones larger than a semi-circle and defining a diameter thereof, the large areas of the plate having lateral edges parallel to the longitudinal axis of the tablet, the distance between the lateral edges being less than the diameters of the rounded end zones.

8. Tablet of claim 6, wherein the bulges have apexes and the semicircular end zones have centers of the circles thereof, with the apexes and the centers of each end lying on a straight line which is perpendicular to the longitudinal axis of the tablet.

9. Tablet of claim 1, wherein the bulges form spherical segments at least in the region of the apexes.

10. Tablet of claim 9, wherein second plates which taper toward the spherical segments form a transition between the spherical segments and the flat plate.

11. Tablet of claim 9, wherein the spherical segments have diameters which are larger than the height of the tablet.

12. Tablet of claim 1, including at least one breaking crevice located in the intervening zone and extending substantially perpendicular to the longitudinal axis of the tablet.

13. Tablet of claim 8, including at least one breaking crevice located in the intervening zone and extending substantially perpendicular to the straight line.

14. Tablet of claim 1, wherein a groove runs over the apex of at least one of the bulges whose projection on one of the large areas of the plate forms at most an acute angle with the longitudinal axis of the table.

15. Tablet of claim 14, wherein the groove has edges with the surface of the bulges, the edges being mirror symmetrical to a plane which is perpendicular to the plate.

16. Elongated, divisible pharmaceutical tablet having an underside, a topside, a longitudinal axis, two ends and an intervening zone therebetween, bulges protruding from the underside and the topside proximate the ends thereof, the width of the tablet at the bulges being greater than at the intervening zone so that when the tablet rests with the underside on a flat surface, the bulges on the underside but not the intervening zone contract the flat surface, the intervening zone having at lease one breaking crevice therein and extending substantially perpendicular to the longitudinal axis.

17. Tablet of claim 16, wherein in one cross-section the tablet is in the form of a dumbbell.

* * * * *